(12) United States Patent
Brown (10) Patent No.: US 9,314,609 B2
(45) Date of Patent: Apr. 19, 2016

(54) DEVICE FOR PROVIDING ELECTRICAL STIMULATION OF A HUMAN KNEE

(71) Applicant: Martin Brown, Farmington, UT (US)

(72) Inventor: Martin Brown, Farmington, UT (US)

( * ) Notice: Subject to any disclaimer, the term of this patent is extended or adjusted under 35 U.S.C. 154(b) by 60 days.

(21) Appl. No.: 13/660,933

(22) Filed: Oct. 25, 2012

(65) Prior Publication Data

US 2013/0110220 A1      May 2, 2013

Related U.S. Application Data

(60) Provisional application No. 61/553,037, filed on Oct. 28, 2011.

(51) Int. Cl.
*A61N 1/04* (2006.01)
*A61N 1/32* (2006.01)
*A61N 1/36* (2006.01)

(52) U.S. Cl.
CPC ............ *A61N 1/0452* (2013.01); *A61N 1/0456* (2013.01); *A61N 1/0484* (2013.01); *A61N 1/326* (2013.01); *A61N 1/36021* (2013.01); *A61N 1/0476* (2013.01)

(58) Field of Classification Search
CPC ............................ A61N 1/321; A61N 1/36021
USPC .............................................. 607/48–51, 149
See application file for complete search history.

(56) References Cited

U.S. PATENT DOCUMENTS

| | | | | |
|---|---|---|---|---|
| 4,381,012 | A | * | 4/1983 | Russek .......................... 600/382 |
| 5,273,033 | A | * | 12/1993 | Hoffman ........................ 607/46 |
| 5,628,722 | A | | 5/1997 | Solomonow et al. |
| 5,766,236 | A | * | 6/1998 | Detty et al. .................... 607/149 |
| 5,976,063 | A | * | 11/1999 | Joutras et al. ................. 482/114 |
| 7,233,828 | B2 | * | 6/2007 | Vlad ............................. 607/148 |
| 7,767,710 | B2 | | 8/2010 | Waddell |

(Continued)

FOREIGN PATENT DOCUMENTS

| | | |
|---|---|---|
| EP | 0302148 | 2/1989 |
| JP | 2011045696 | 3/2011 |

(Continued)

OTHER PUBLICATIONS

International Search Report and Written Opinion of the International Searching Authority (for a PCT application containing the same claims as the current application).

(Continued)

*Primary Examiner* — Christopher D Koharski
*Assistant Examiner* — Michael D Abreu
(74) *Attorney, Agent, or Firm* — Maschoff Brennan (57) ABSTRACT

A device for providing electrical stimulation of a human knee. One example device includes first, second, third, and fourth surface electrodes, a wrap configured to be wrapped around the human knee, and an electrical device. The wrap includes a wrap positioning indicator configured to be positioned over a specified portion of the human knee. The wrap also includes first, second, third, and fourth electrode attachment locations corresponding to acupuncture points Stomach 34, Stomach 36, Spleen 9, and Spleen 10. The electrical device is configured to automatically send, to the first, second, third, and fourth surface electrodes, during a single treatment, a first current at a first frequency for a first time period followed by a second current at a second frequency for a second time period, with the first frequency being different from the second frequency.

23 Claims, 5 Drawing Sheets

(56) References Cited

U.S. PATENT DOCUMENTS

| | | | |
|---|---|---|---|
| 8,285,381 B2* | 10/2012 | Fahey | 607/48 |
| 2004/0054379 A1 | 3/2004 | Carroll et al. | |
| 2007/0038252 A1* | 2/2007 | Carroll | 607/2 |
| 2007/0112393 A1* | 5/2007 | Gliner | 607/45 |
| 2007/0197946 A1 | 8/2007 | Gilmour | |
| 2007/0265680 A1 | 11/2007 | Liu | |
| 2008/0288035 A1 | 11/2008 | Gill et al. | |
| 2009/0287126 A1 | 11/2009 | Skahan et al. | |
| 2010/0137939 A1* | 6/2010 | Liu | 607/46 |
| 2010/0145410 A1 | 6/2010 | Kirsch et al. | |
| 2010/0262052 A1 | 10/2010 | Lunau et al. | |
| 2010/0324626 A1 | 12/2010 | Lefkovitz | |
| 2013/0085317 A1* | 4/2013 | Feinstein | 600/14 |

FOREIGN PATENT DOCUMENTS

| | | |
|---|---|---|
| KR | 10-2010-0024265 | 3/2010 |
| WO | 2007019569 | 2/2007 |

OTHER PUBLICATIONS

Extended European Search Report dated Feb. 13, 2015, as received in Application No. 12843388.5 (5 pgs).

DeSantana et al., "Effectiveness of Transcutaneous Electrical Nerve Stimulation for Treatment of Hyperalgesia and Pain" Sep. 18, 2009 available at: http://www.ncbi.nlm.nih.ciov/pmc/articles/PMC2746624/ (11 pgs).

'New York Chiropractic College: Chapter 4—Physiologic Therapeutics—ElectricalStimulating Currents' Sep. 10, 2010 (Oct. 9, 2010) available at:http://www,nvcc.edu/webdocs/ic/IQA/IQAFiles/Protocols/Chapter4/ElectricalStimulatinciCurrents4 4.pdf (10 pgs).

Office Action mailed Nov. 16, 2015 in Canadian Patent Application No. 2853419 (5 pgs).

Odell, et al., "Anti-inflammatory Effects of Electronic Signal Treatment", Pain Physician 2008; 11:891-907 • ISSN 1533-3159 (18 pgs).

Malemud, C.J., Anticytokine therapy for osteoarthritis: evidence to date, Drugs Aging. Feb. 1, 2010;27(2):95-115. doi: 10.2165/11319950-000000000-00000 (22 pgs).

Ahsin et al., "Clinical and endocrinological changes after electroacupuncture treatment in patients with osteoarthritis of the knee", Pain. Dec. 15, 2009;147(1-3):60-6. doi: 10.1016/j.pain.2009.08.004. Epub Sep. 18, 2009. (7 pgs).

Fary, Robyn E et al. "The Effectiveness of Pulsed Electrical Stimulation (E-PES) in the Management of Osteoarthritis of the Knee: A Protocol for a Randomised Controlled Trial." BMC Musculoskeletal Disorders 9 (2008): 18. PMC. Web. Feb. 10, 2016 (10 pgs).

Huang et al., "Effects of electroacupuncture on synovia free radicals in rabbits with knee osteoarthritis", avaialable at: https://www.researchgate.net/publication/51405328_Effects_of_electroacupuncture_on_synovia_free_radicals_in_rabbits_with_knee_osteoarthritis accessed Feb. 9, 2016 (3 pgs).

Ouyang et al., "Effect of electro-acupuncture on tumor necrosis factor-α and vascular endothelial growth factor in peripheral blood and joint synovia of patients with rheumatoid arthritis", available at http://www.ncbi.nlm.nih.gov/pubmed/21725875, accessed Feb. 9, 2016 (2 pgs).

Boston et al., "Acupuncture Provides Added Benefit for People With Osteoarthritis of the Knee", Dec. 20, 2004, Study by University of Maryland doctors is one of the largest ever for acupuncture (1 page).

Ng et al., "The Effects of Electro-Acupuncture and Transcutaneous Electrical Nerve Stimulation on Patients with Painful Osteoarthritic Knees: A Randomized Controlled Trial with Follow-Up Evaluation", The Journal of Alternative and Complementary Medicine, vol. 9, No. 5, 2003, pp. 641-649.

Wu et al., Experimental study of low-frequency electroacupuncture-induced differentiation of bone marrow mesenchymal stem cells into chondrocytes, International Journal of Molecular Medicine 27: 79-86, 2011.

Smith et al., "Synovial membrane inflammation and cytokine production in patients with early osteoarthritis" The Journal of Rheumatology [1997, 24(2):365-371].

Lawrence et al., "Emerging ideas: prevention of posttraumatic arthritis through interleukin-1 and tumor necrosis factor-alpha inhibition", Clin Orthop Relat Res. Dec. 2011;469(12):3522-6. doi: 10.1007/s11999-010-1699-4. Epub Dec. 16, 2010.

Hiraoka et al."Mild electrical stimulation with heat stimulation increase heat shock protein 70 in articular chondrocyte", J Orthop Res. Jun. 2013;31(6):894-900. doi: 10.1002/jor.22307. Epub Jan. 17, 2013.

Reviewed by David Zelman, MD, "Alternative to Knee Osteoarthritis Treatment", available at: http://www.webmd.com/osteoarthritis/guide/optionsbasics?page=4, accessed Feb. 9, 2016.

Selfe et al., "Acupuncture and Osteoarthritis of the Knee: A Review of Randomized, Controlled Trials." Family & community health 31.3 (2008): 247-254. PMC. Web. Feb. 10, 2016.

Fary, Robyn E et al. "The Effectiveness of Pulsed Electrical Stimulation (E-PES) in the Management of Osteoarthritis of the Knee: A Protocol for a Randomised Controlled Trial." BMC Musculoskeletal Disorders 9 (2008): 18. PMC. Web. Feb. 10, 2016.

* cited by examiner

DEVICE FOR PROVIDING ELECTRICAL STIMULATION OF A HUMAN KNEE

CROSS-REFERENCE TO RELATED APPLICATIONS

This application claims the benefit of and priority to U.S. Provisional Patent Application Ser. No. 61/553,037 filed on Oct. 28, 2011, which application is incorporated herein by reference in its entirety.

BACKGROUND OF THE INVENTION

Chronic knee and joint pain is an affliction that affects millions of people. Often, there is little or no treatment available to eliminate the pain. I.e., the pain sufferer is forced to control the pain using medications rather than eliminating the pain and enjoying long term relief. Alternatively, the sufferer can undergo surgery or other treatment which may be risky.

One possible treatment for the sufferer is acupuncture. Acupuncture consists of needle insertions at specified locations. Acupuncture may relieve the pain but it requires a highly trained specialist. If the practitioner is inexperienced the treatment may cause more damage than it relieves. In addition, acupuncture may be very time consuming, requiring a large time commitment from the patient. This is especially problematic if the sufferer requires more than a single round of treatment.

Another possible treatment available to the sufferer is surgery. However, surgery can also be time consuming. In addition, surgery can lead to other problems such as infection and secondary problems as the sufferer favors the joint while recovering from surgery. Further, the recovery time for surgery may be significant and may include supplemental treatments such as physical therapy other rounds of surgery in order to complete treatment.

A third possible treatment is the use of pharmaceuticals such as anti-inflammatories. However, these often mask the problem by reducing the swelling of the joint and/or the pain in the joint. This means that the sufferer may not seek appropriate medical attention to ensure that the underlying problem is corrected. This may mean that the sufferer has more extensive damage to the joint before treatment is sought, leading to additional problems.

Accordingly, there is a need in the art for a treatment for joint pain that is effective both in the short term and in the long term. In addition, there is a need in the art for the treatment to be available for use at home. Further, there is a need in the art for a treatment protocol that equals or surpasses the effectiveness of current pharmelectrical therapy.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a device for providing electrical stimulation of a human knee. The device includes first, second, third, and fourth surface electrodes, a wrap configured to be wrapped around the human knee, and an electrical device. The wrap includes a wrap positioning indicator configured to be positioned over a specified portion of the human knee in order to properly position the wrap around the human knee. The wrap also includes first, second, third, and fourth electrode attachment locations. The first electrode attachment location is configured to have the first surface electrode attached thereto so as to position the first surface electrode on the skin over acupuncture point Stomach 34 when the wrap is properly positioned around the human knee. The second electrode attachment location is configured to have the second surface electrode attached thereto so as to position the second surface electrode on the skin over acupuncture point Stomach 36 when the wrap is properly positioned around the human knee. The third electrode attachment location is configured to have the third surface electrode attached thereto so as to position the third surface electrode on the skin over acupuncture point Spleen 9 when the wrap is properly positioned around the human knee. The fourth electrode attachment location is configured to have the fourth surface electrode attached thereto so as to position the fourth surface electrode on the skin over acupuncture point Spleen 10 when the wrap is properly positioned around the human knee. The electrical device is configured to automatically send, to the first, second, third, and fourth surface electrodes, during a single treatment, a first current followed by a second current. The electrical device is configured to send the first current at a first frequency for a first time period and send the second current at a second frequency for a second time period, with the first frequency being different from the second frequency.

Another example embodiment includes a device for providing electrical stimulation of a human knee. The device includes first, second, third, and fourth surface electrodes, a template for placement of the electrodes for use in electrical stimulation of the human knee, and an electrical device. The template includes a template positioning indicator configured to be positioned over a specified portion of the human knee in order to properly position the template over the human knee. The template also includes first, second, third, and fourth electrode placement indicators. The first electrode placement indicator is configured for positioning a first surface electrode on the skin over acupuncture point Stomach 34 when the template is properly positioned around the human knee. The second electrode placement indicator is configured for positioning a second surface electrode on the skin over acupuncture point Stomach 36 when the template is properly positioned around the human knee. The third electrode placement indicator is configured for positioning a third surface electrode on the skin over acupuncture point Spleen 9 when the template is properly positioned around the human knee. The fourth electrode placement indicator is configured for positioning a fourth surface electrode on the skin over acupuncture point Spleen 10 when the template is properly positioned around the human knee. The electrical device is configured to automatically send, to the first, second, third, and fourth surface electrodes, during a single treatment, a first current followed by a second current. The electrical device is configured to send the first current at a first frequency for a first time period and send the second current at a second frequency for a second time period, with the first frequency being different from the second frequency.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1:
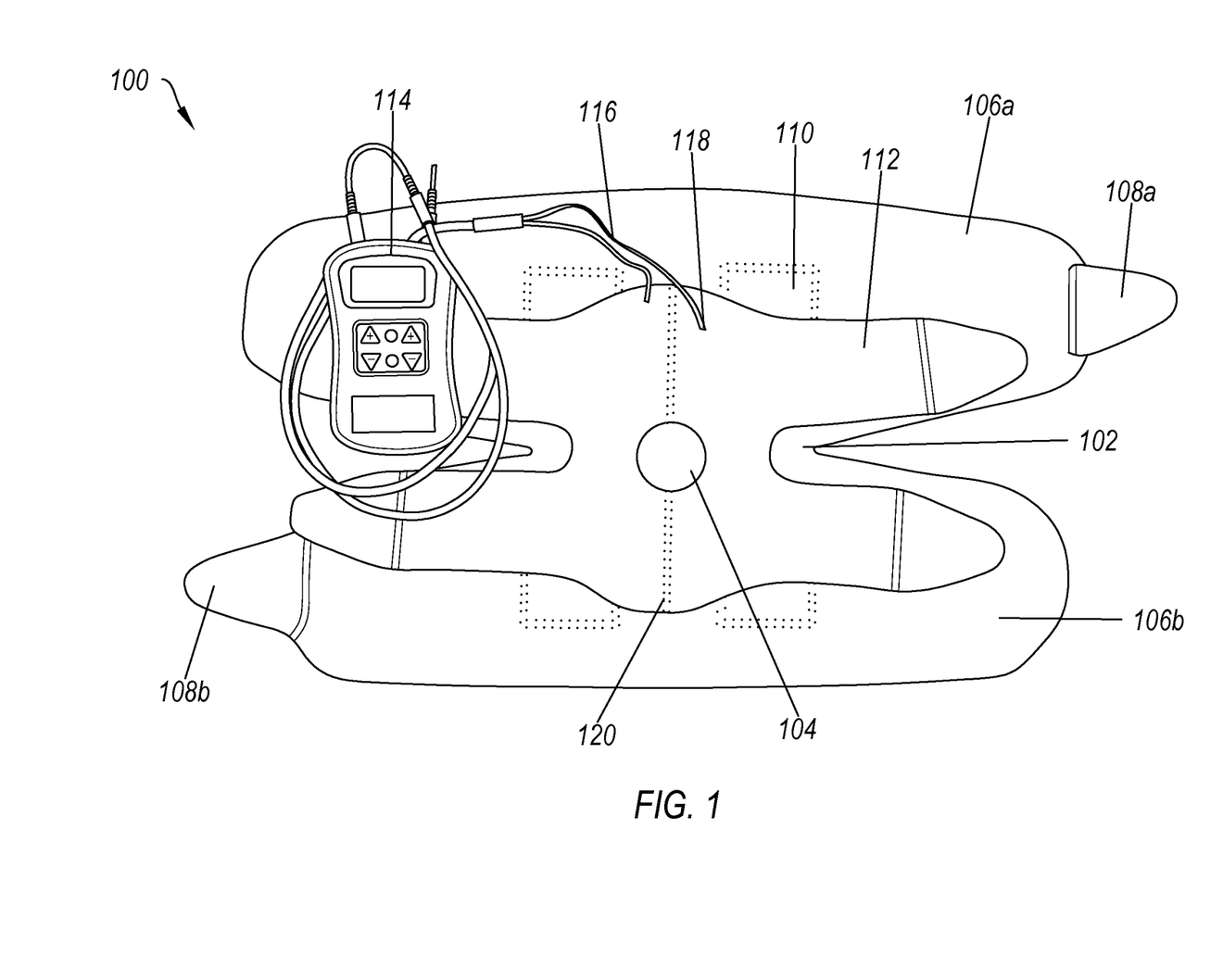
FIG. 1 illustrates a wrap for placing electrodes.

FIG. 1 illustrates a wrap 100 for treating joint pain. In at least one implementation, the wrap 100 can be placed in the appropriate location and automatically locate attached electrodes in the proper location. I.e., the wrap 100 can allow a user to place the electrodes without assistance. This can allow the user to undergo the treatment at home and without medical supervision.

FIG. 1 shows that the wrap 100 can include a body 102. In at least one implementation, the body 102 can include the central portion of the wrap 100. In particular, the body 102 can be placed over the joint. This can allow the user to easily identify if the wrap 100 can has been placed correctly. Additionally or alternatively, the body 102 can ensure that the wrap 100 is of appropriate size and/or shape.

FIG. 1 also shows that the wrap 100 can include a center hole 104. In at least one implementation, the center hole 104 can be located in the body 102. The center hole 104 can be used to center the wrap 100. For example, the center hole 104 can be placed over a specified portion of the joint, such as the patella for the knee. The center hole 104 can be indicative of a center point, such as a round hole, or shaped and sized to fit over the joint.

FIG. 1 further shows that the wrap 100 can include a first arm 106a and a second arm 106b (collectively "arms 106"). In at least one implementation, the first arm 106a can be configured to be placed on a first side of the joint and the second arm 106b can be configured to be placed on a second side of the joint. In particular, the arms 106 can secure the wrap 100 relative to the joint to allow the treatment to proceed as desired. For example, the first arm 106a can be placed on the upper arm for elbow treatment or on the upper leg for knee treatment and the second arm 106b can be placed on the lower arm or lower leg.

FIG. 1 additionally shows that the wrap 100 arm can include a first attachment 108a and a second attachment 108b (collectively "attachments 108") on the first arm 106a and the second arm 106b, respectively. In at least one implementation, the attachments 108 can be configured to secure the arms in place relative to the joint. In particular, the attachments 108 can releasably attach the arms 106 at the desired tension, allowing the user to place the wrap without making the wrap 100 too tight, which could inhibit circulation, or too loose, which could allow the wrap 100 to move relative to the joint. For example, the attachments 108 can include a hook and loop fastener, a button, a snap, a clip or any other desired attachment mechanism.

FIG. 1 moreover shows that the wrap 100 can include electrode locators 110. In at least one implementation, electrode locators 110 can allow the user to insert the desired electrodes. For example the electrode locators 110 can include a pouch or pocket or other mechanism for receiving the desired electrode. For example, the electrode locators 110 can include an indicator, such as a tag or label, that indicates the electrode to be inserted based on the joint. E.g., a positive electrode could be placed in a particular location for treatment of the right knee, but that same location would require a negative location for the left knee and vice versa. Additionally or alternatively, the electrode locators 110 can ensure that the electrodes are placed correctly relative to the joint. For example, the first arm 106a can include an electrode locator 110 on either branch of the first arm 106a, to be placed over the acupuncture points Stomach 34 and Spleen 10 and an electrode locator 110 on either branch of the second arm 106b, to be placed over acupuncture points Stomach 36 and Spleen 9.

In at least one implementation, the wrap 100 can be used to treat joints on both the right side and the left side of the user's body. In particular, the current can flow from positive to negative electrodes away from the user's trunk on the inside of the user's limb and toward the user's trunk on the outside of the of the user's limb. Additionally or alternatively, the current can flow from positive to negative electrodes away from the user's trunk on the outside of the user's limb and toward the user's trunk on the inside of the of the user's limb. The electrodes can be reversed to treat the same joint on the other side of the user's body.

FIG. 1 also shows that the wrap 100 can include a cover 112. In at least one implementation, the cover 112 can allow access to the electrode locators 110. In particular, the cover 112 can be closed to prevent access to the electrode locators 110 or opened to allow access to the electrode locators 110. In particular, the cover 112 can be releasably attached to the body 102, the first arm 106a or the second arm 106b to prevent access to the electrodes during use.

FIG. 1 further shows that the wrap 100 can include a control 114. In at least one implementation, the control 114 can provide electrical power to the electrodes. In particular, the control 114 can provide the power in the desired sequence and timing to provide treatment to the joint.

FIG. 1 additionally shows that the wrap 100 can include one or more leads 116. In at least one implementation the leads 116 can transfer electrical power from the control 114 to the electrodes. I.e., the leads 116 can include wires or other mechanisms from transferring electrical power from the control 114 to the electrodes.

FIG. 1 moreover shows that wrap 100 can include a lead guide 118. In at least one implementation, the lead guide 118 can position the leads 116. In particular, the lead guide 118 can position the leads 116 such that they remain connected and/or are protected from damage during use.

FIG. 1 also shows that the wrap 100 can include a centerline 120. In at least one implementation, the centerline 100 can include a permanent attachment between the body 102 and the cover 112. Additionally or alternatively, the centerline 120 can serve as a guide, further directing the leads 114 to the correct position to attach to the electrodes.

Figure 2:
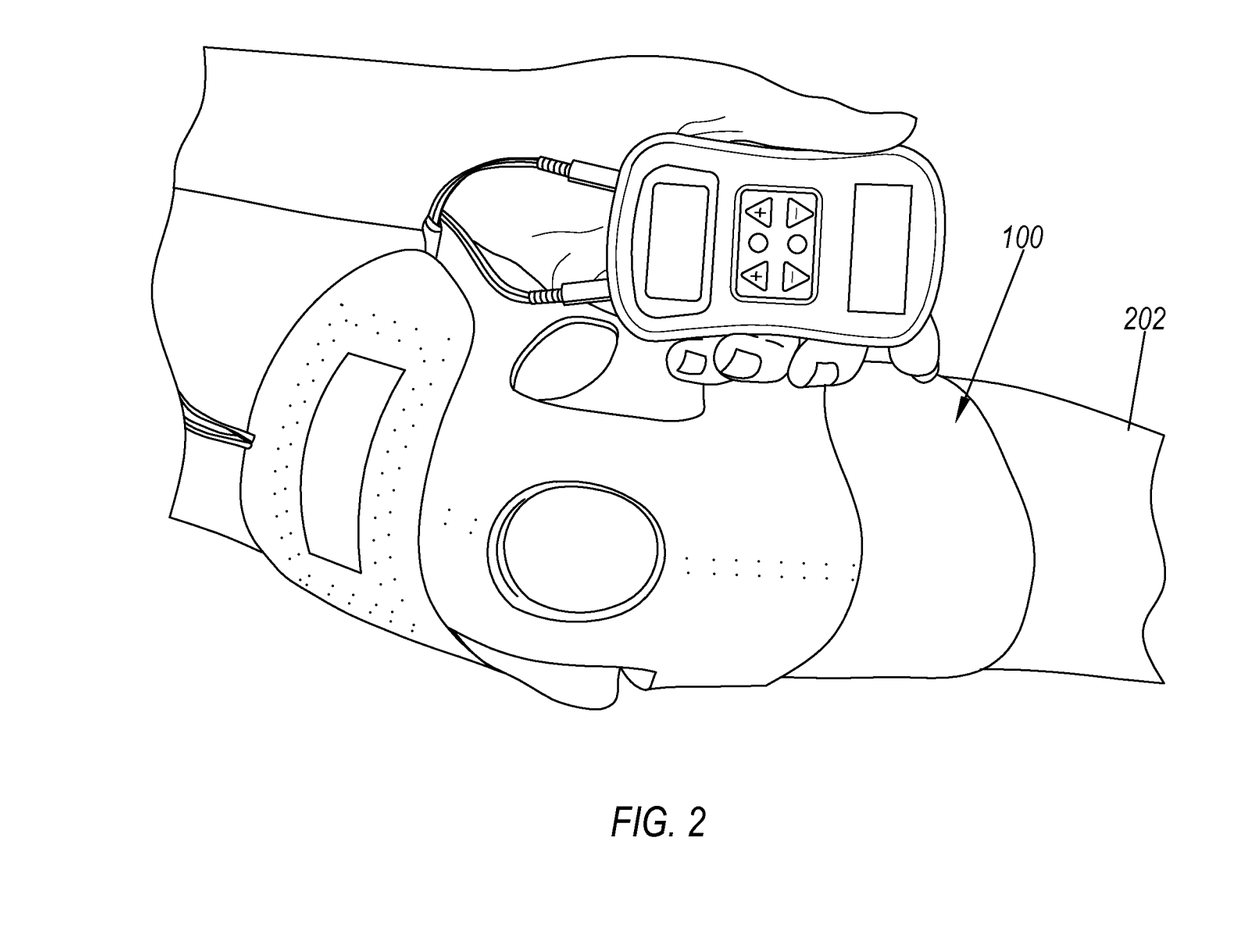
FIG. 2 illustrates an example of a wrap in use.

FIG. 2 illustrates an example of a wrap 100 in use. In at least one implementation, the wrap 100 can be secured over a joint of a user 202 in the desired location. Once the wrap 100 has been placed in the correct location, the electrodes will be in the preferred location for treatment. Additionally or alternatively, the wrap 100 can provide compression treatment to the joint simultaneous with the electrostimulation.

Figure 3:
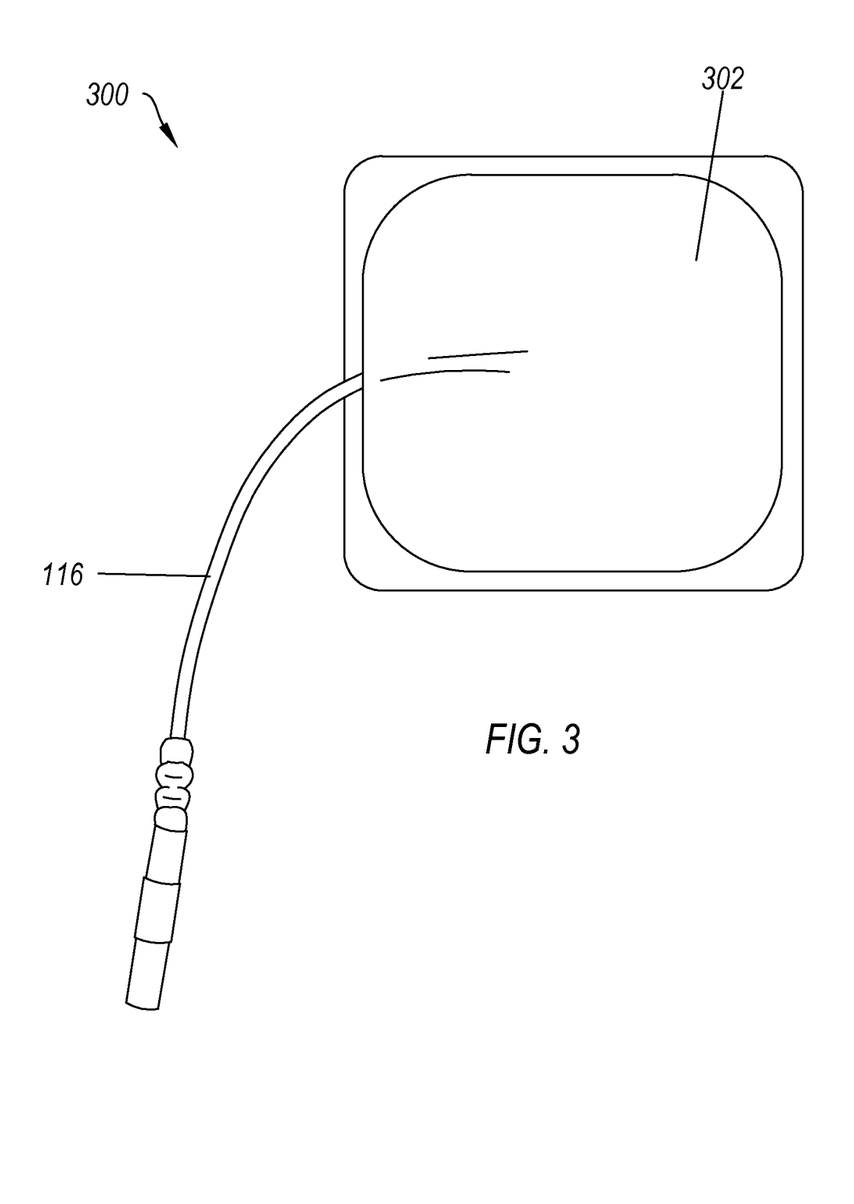
FIG. 3 illustrates an example of an electrode.

FIG. 3 illustrates an example of an electrode 300. In at least one implementation, the electrode 300 can be configured to deliver electrical stimulation to the desired location. In particular, the electrode 300 can provide a voltage difference at different locations on the user, causing an electric current to flow through the skin and underlying tissue of the user.

FIG. 3 shows that the electrode 300 can include a pad 302. In at least one implementation, the pad 302 is configured to apply an electrical current to the skin of the user. In particular, the pad 302 is configured to be placed on or near the skin of the user. A current delivered to the pad 302 via the lead 116 is then transferred to the underlying tissue of the user.

In at least one implementation, the electrical stimulation can include transcutaneous electrical nerve stimulation (TENS). TENS is the use of electric current produced by a device to stimulate the nerves for therapeutic purposes. In particular, the electrical stimulation can include electrical stimulation applied to the skin of the user, which then stimulates the underlying muscle and nervous tissue.

Figure 4A:
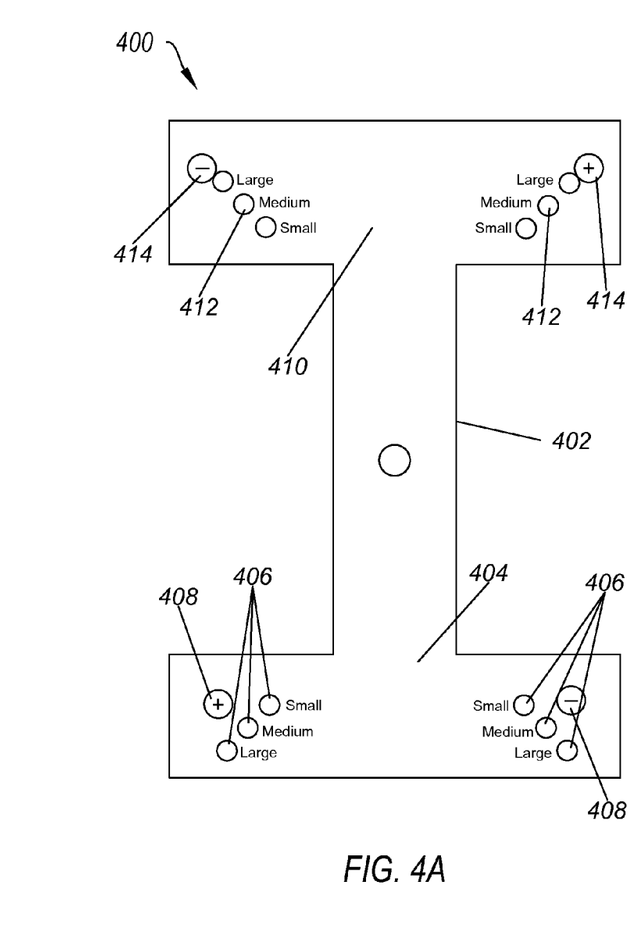
FIG. 4A illustrates a top view of the template for placing electrodes.
Figure 4B:
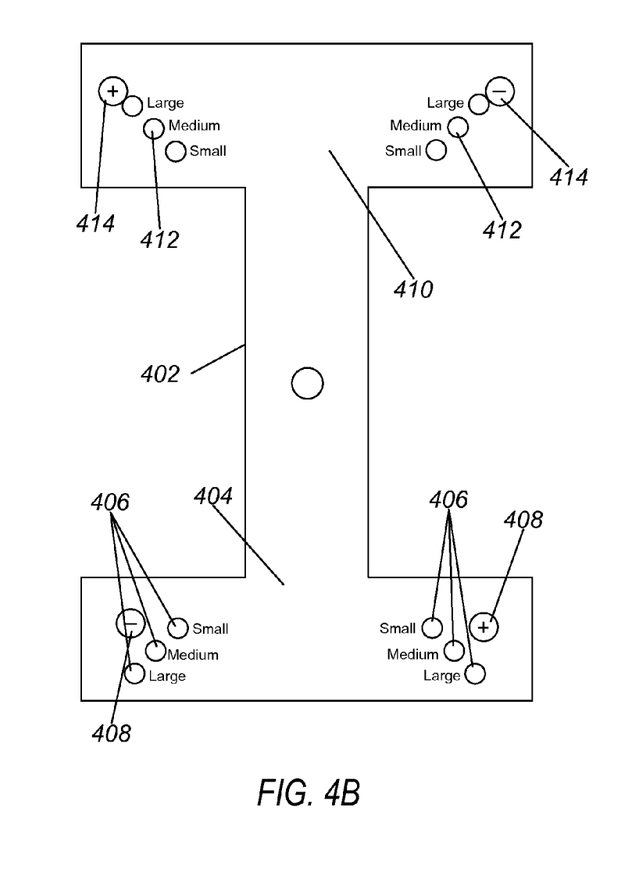
FIG. 4B illustrates a bottom view of the template for placing electrodes.

FIGS. 4A and 4B illustrate a template 400 for placing electrodes. FIG. 4A illustrates a top view of the template 400 for placing electrodes; and FIG. 4B illustrates a bottom view of the template 400 for placing electrodes. In at least one implementation, the template 400 can ensure that a user can place the electrodes in the correct position without compression treatment of the joint. In particular, the template 400 can allow a user to place the electrodes without assistance. This can allow the user to undergo the treatment at home and without medical supervision. For example, the user can place the electrodes on his/her right knee with the surface shown in FIG. 4A away from his/her skin and can place the electrodes on his/her left knee with the surface shown in FIG. 4B away from his/her skin.

FIGS. 4A and 4B show that the template 400 can include a body 402. In at least one implementation, the body 402 can include the central portion of the template 400. In particular, the body 402 can be placed over the joint. This can allow the user to easily identify if the template 400 can has been placed correctly. Additionally or alternatively, the body 402 can ensure that the template 400 is of appropriate size and/or shape.

FIGS. 4A and 4B also show that the template 400 can include a center hole 404. In at least one implementation, the center hole 404 can be located in the body 402. The center hole 404 can be used to center the template 400. For example, the center hole 404 can be placed over a specified portion of the joint, such as the patella for the knee. The center hole 404 can be indicative of a center point, such as a round hole, or shaped and sized to fit over the joint.

FIGS. 4A and 4B also shows that the template 400 can include a first arm 406. In at least one implementation, the first arm 406 can be configured to be placed on a first side of the joint. For example, the first arm 406 can be placed on the upper arm for elbow treatment or on the upper leg for knee treatment. The first arm 406 can include one or more location indicators 408. For example, the first arm 406 can include a location indicator 408 at either end of the first arm 406. The location indicators 408 can identify the acupuncture points Stomach 34 and Spleen 10 . In addition, the one or more location indicators 408 can be used to determine the correct location for electrode placement in small, medium and large sizes. The first arm 406 can also include one or more polarity indicators 410. In at least one implementation, the one or more polarity indicators 410 can indicate which electrode should be placed on which location indicator 408.

FIGS. 4A and 4B further shows that the template 400 can include a second arm 412. In at least one implementation the second arm 412 can be configured to be placed on a second side of the joint. For example, the second arm 412 can be placed on the lower arm for elbow treatment or on the lower leg for knee treatment. The second arm 412 can include one or more locations indicators 414. For example, the second arm 412 can include a location indicator 414 at either end of the second arm 412. The location indicators 414 can identify the acupuncture points Stomach 36 and Spleen 9. In addition, the one or more location indicators 414 can be used to determine the correct location for electrode placement in small, medium and large sizes. The second arm 412 can also include one or more polarity indicators 416. In at least one implementation, the one or more polarity indicators 416 can indicate which electrode should be placed on which location indicator 416.

In at least one implementation, the template 400 can be used to treat joints on both the right side and the left side of the user's body. In particular, the current can flow from positive to negative electrodes away from the user's trunk on the inside of the user's limb and toward the user's trunk on the outside of the of the user's limb. I.e., the template 400 in the configuration shown in FIGS. 4A and 4B can be used to treat joints on the right side of the user's body. Additionally or alternatively, the template 400 can be turned over about the long axis of the body 402 for treatment on the user's left side. This can maintain the current flow away from the user's trunk on the inside of the user's limb and toward the user's trunk on the outside of the of the user's limb.

Figure 5:
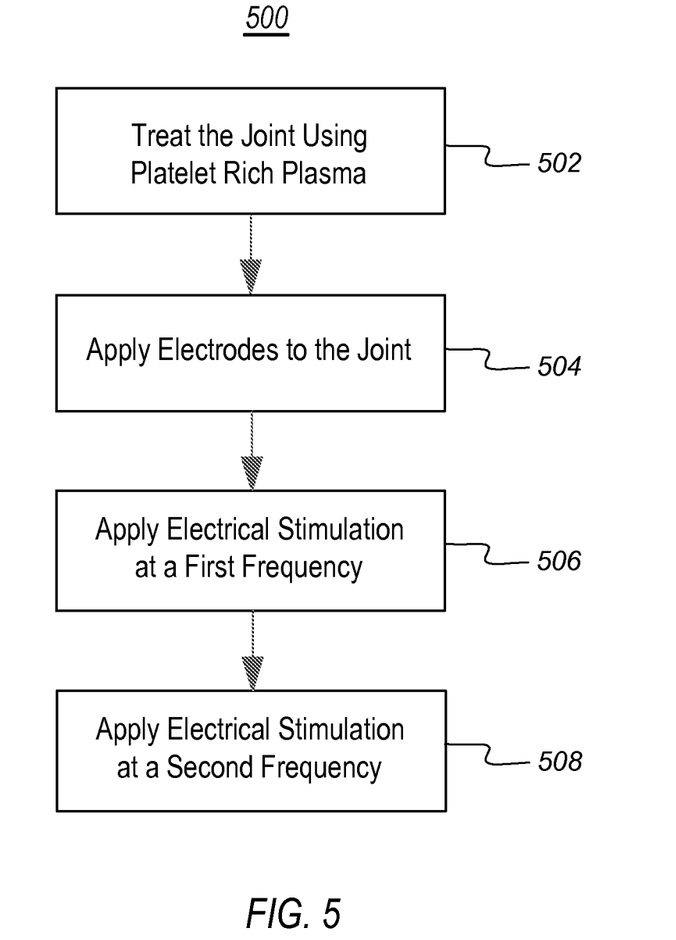
FIG. 5 is a flow chart illustrating a method of treating a joint injury.

FIG. 5 is a flow chart illustrating a method 500 of treating a joint injury. In at least one implementation, the method 500 can include electrical stimulation of the joint. In particular, the method 500 can include electostimulation of a joint, such as an elbow or a knee, for the reduction or elimination of pain within the joint.

FIG. 5 shows that the treatment method 500 can include treating 502 the joint with platelet rich plasma (PRP). PRP is blood plasma that has been enriched with platelets. As a concentrated source of autologous platelets, PRP contains (and releases through degranulation) several different growth factors and other cytokines that stimulate healing of bone and soft tissue. The efficacy of certain growth factors in healing various injuries and the concentrations of these growth factors found within PRP are the theoretical basis for the use of PRP in tissue repair. The platelets collected in PRP are activated by the addition of thrombin and calcium chloride, which induces the release of these factors from alpha granules. The growth factors and other cytokines present in PRP may include: platelet-derived growth factor; transforming growth factor beta; fibroblast growth factor; insulin-like growth factor 1; insulin-like growth factor 2; vascular endothelial growth factor; epidermal growth factor; Interleukin 8; keratinocyte growth factor; and connective tissue growth factor. There are, at present, two methods of PRP preparation approved by the U.S. Food and Drug Administration. Both processes involve the collection of whole blood that is anticoagulated with citrate dextrose) before undergoing two stages of centrifugation designed to separate the PRP aliquot from platelet-poor plasma and red blood cells. In humans, the typical baseline blood platelet count is approximately 200, 000 per μL; therapeutic PRP concentrates the platelets by roughly five-fold. There is however broad variability in the production of PRP by various concentrating equipment and techniques.

FIG. 5 also shows that the treatment method 500 can include applying 504 electrodes to the joint. In at least one implementation, the electrodes can be applied 504 in a specified location using the wrap 100 of FIG. 1 or the template 400 of FIGS. 4A and 4B. In particular, the electrodes can be applied 504 to acupuncture points around the joint. Additionally or alternatively, the direction of current flow, as directed by the electrode placement, can aid in the healing process.

FIG. 5 further shows that the treatment method 500 can include applying 506 electrical stimulation at a first frequency. The first frequency can be any desired therapeutic frequency. For example, the first frequency can be between 120 and 180 Hz. In particular, the first frequency can be approximately 150 Hz. Additionally or alternatively, the first frequency can be between 80 and 120 Hz. In particular, the first frequency can be approximately 100 Hz. The first frequency can be applied for a first time period. For example, the first frequency can be applied for between 15 and 30 minutes. Additionally or alternatively, the time period can be between 6 and 8 hours. The first frequency can be applied for a specific pulse width. I.e., the first frequency can be applied in an "on/off" pattern with a specific period. For example, the pulse width can be between 180 and 250 microseconds. The first frequency can be applied with a current at a subthreshold level. I.e., the current can be small enough that the user cannot perceive the current. For example, the current can be less than 1 mA (milliamp). Additionally or alternatively, the current can be small enough to prevent disruption of cellular production of Adenosine triphosphate (ATP). For example, the current can be between 50 and 1000 microamps. As used in the specification and the claims, the term approximately shall mean that the value is within 10% of the stated value, unless otherwise specified.

FIG. 5 additionally shows that the treatment method 500 can include applying 508 electrical stimulation at a second frequency. The second frequency can be any desired therapeutic frequency. For example, the second frequency can be between 1 and 3 Hz. In particular, the second frequency can be approximately 2 Hz. The second frequency can be applied for a second time period. The second time period can be the same as the first time period or a different amount of time. For example, the second frequency can be applied for between 15 and 30 minutes. The second frequency can be applied for a specific pulse width. The second pulse width can have the same period as the same as the first pulse width or a different period. For example, the pulse width can be between 180 and 250 microseconds.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for providing electrical stimulation of a human knee, the device comprising:
    first, second, third, and fourth surface electrodes;
    a template for placement of the electrodes for use in electrical stimulation of the human knee;
    a template positioning indicator included in the template and configured to be positioned over a specified portion of the human knee in order to properly position the template over the human knee;
    a first electrode placement indicator included in the template and configured for positioning a first surface electrode on the skin over acupuncture point Stomach 34 when the template is properly positioned around the human knee;
    a second electrode placement indicator included in the template and configured for positioning a second surface electrode on the skin over acupuncture point Stomach 36 when the template is properly positioned around the human knee;
    a third electrode placement indicator included in the template and configured for positioning a third surface electrode on the skin over acupuncture point Spleen 9 when the template is properly positioned around the human knee;
    a fourth electrode placement indicator included in the template and configured for positioning a fourth surface electrode on the skin over acupuncture point Spleen 10 when the template is properly positioned around the human knee; and
    an electrical device configured to automatically send, to the first, second, third, and fourth surface electrodes, during a single treatment, a first current followed by a second current, the electrical device configured to send the first current at a first frequency for a first time period, the electrical device configured to send the second current at a second frequency for a second time period, the first frequency being different from the second frequency.

2. The device of claim 1, further comprising:
    a first electrode polarity indicator proximate the first electrode placement indicator;
    a second electrode polarity indicator proximate the second electrode placement indicator;
    a third electrode polarity indicator proximate the third electrode placement indicator; and
    a fourth electrode polarity indicator proximate the fourth electrode placement indicator.

3. The device of claim 2, wherein:
    the first and third electrode polarity indicators are negative and the second and fourth electrode polarity indicators are positive; and
    the template is reversible with first and second sides, the first side corresponding to a right human knee and the second side corresponding to a left human knee.

4. The device of claim 2, wherein each of the first, second, third, and fourth electrode placement indicators includes:
    a small human knee electrode placement indicator configured for use where the human knee is relatively small-sized;
    a medium human knee electrode placement indicator configured for use where the human knee is relatively medium-sized; and
    a large human knee electrode placement indicator configured for use where the human knee is relatively large-sized.

5. The device of claim 1, wherein:
the template positioning indicator is a hole defined in the template;
the first and fourth electrode placement indicators are holes defined in the template; and
the second and third electrode placement indicators are holes defined in the template.

6. The device of claim 1, wherein:
the first frequency is between 90 and 160 Hz; and
the second frequency is between 2 and 6 Hz.

7. The device of claim 1, wherein:
the first frequency is approximately 150 Hz; and
the second frequency is approximately 2 Hz.

8. The device of claim 1, wherein:
the first time period is between 15 and 30 minutes; and
the second time period is between 15 and 30 minutes.

9. The device of claim 1, wherein:
the first time period is approximately 15 minutes; and
the second time period is approximately 15 minutes.

10. The device of claim 1, wherein the first current and the second current are sent at a pulse width of between 180 and 250 microseconds.

11. The device of claim 1, wherein the first current and the second current are sent at a pulse width of approximately 180 microseconds.

12. The device of claim 1, wherein:
the first frequency is approximately 150 Hz;
the second frequency is approximately 2 Hz;
the first time period is approximately 15 minutes;
the second time period is approximately 15 minutes;
the first surface electrode is configured to have a negative polarity;
the second surface electrode is configured to have a positive polarity;
the third surface electrode is configured to have a negative polarity; and
the fourth surface electrode is configured to have a positive polarity.

13. A device for providing electrical stimulation of a human knee, the device comprising:
first, second, third, and fourth surface electrodes;
a wrap configured to be wrapped around the human knee;
a wrap positioning indicator included in the wrap and configured to be positioned over a specified portion of the human knee in order to properly position the wrap around the human knee;
a first electrode attachment location included in the wrap and configured to have the first surface electrode attached thereto so as to position the first surface electrode on the skin over acupuncture point Stomach 34 when the wrap is properly positioned around the human knee;
a second electrode attachment location included in the wrap and configured to have the second surface electrode attached thereto so as to position the second surface electrode on the skin over acupuncture point Stomach 36 when the wrap is properly positioned around the human knee;
a third electrode attachment location included in the wrap and configured to have the third surface electrode attached thereto so as to position the third surface electrode on the skin over acupuncture point Spleen 9 when the wrap is properly positioned around the human knee;
a fourth electrode attachment location included in the wrap and configured to have the fourth surface electrode attached thereto so as to position the fourth surface electrode on the skin over acupuncture point Spleen 10 when the wrap is properly positioned around the human knee; and
an electrical device configured to automatically send, to the first, second, third, and fourth surface electrodes, during a single treatment, a first current followed by a second current, the electrical device configured to send the first current at a first frequency for a first time period, the electrical device configured to send the second current at a second frequency for a second time period, the first frequency being different from the second frequency.

14. The device of claim 13, further comprising:
a first negative polarity indicator proximate the first electrode attachment location;
a first positive polarity indicator proximate the second electrode attachment location;
a second negative polarity indicator proximate the third electrode attachment location; and
a second positive polarity indicator proximate the fourth electrode attachment location.

15. The device of claim 13, wherein the wrap includes first and second configurations, with the first configuration corresponding to a right human knee and the second configuration corresponding to a left human knee.

16. The device of claim 13, wherein each of the first, second, third, and fourth electrode attachment locations includes:
a small human knee electrode attachment location configured for use where the human knee is relatively small-sized;
a medium human knee electrode attachment location configured for use where the human knee is relatively medium-sized; and
is a large human knee electrode attachment location configured for use where the human knee is relatively large-sized.

17. The device of claim 13, wherein:
the first frequency is between 90 and 160 Hz; and
the second frequency is between 2 and 6 Hz.

18. The device of claim 13, wherein:
the first frequency is approximately 150 Hz; and
the second frequency is approximately 2 Hz.

19. The device of claim 13, wherein:
the first time period is between 15 and 30 minutes; and
the second time period is between 15 and 30 minutes.

20. The device of claim 13, wherein:
the first time period is approximately 15 minutes; and
the second time period is approximately 15 minutes.

21. The device of claim 13, wherein the first current and the second current are sent at a pulse width of between 180 and 250 microseconds.

22. The device of claim 13, wherein the first current and the second current are sent at a pulse width of approximately 180 microseconds.

23. The device of claim 13, wherein:
the first frequency is approximately 150 Hz;
the second frequency is approximately 2 Hz;
the first time period is approximately 15 minutes;
the second time period is approximately 15 minutes;
the first surface electrode is configured to have a negative polarity;
the second surface electrode is configured to have a positive polarity;
the third surface electrode is configured to have a negative polarity; and the fourth surface electrode is configured to have a positive
polarity.

\* \* \* \* \*